United States Patent
Zamierowski

(10) Patent No.: US 10,420,847 B2
(45) Date of Patent: Sep. 24, 2019

(54) SYSTEM AND METHOD FOR WOUND ARRAY VARIABLES EVALUATION (WAVE)

(71) Applicant: Zam Research LLC, Overland Park, KS (US)

(72) Inventor: David S. Zamierowski, Overland Park, KS (US)

(73) Assignee: University of Kansas Medical Center Research Institute, Inc., Kansas City, MO (US)

( * ) Notice: Subject to any disclaimer, the term of this patent is extended or adjusted under 35 U.S.C. 154(b) by 578 days.

(21) Appl. No.: 14/985,229

(22) Filed: Dec. 30, 2015

(65) Prior Publication Data

US 2017/0189555 A1    Jul. 6, 2017

(51) Int. Cl.
*A61K 49/00* (2006.01)
*A61D 9/00* (2006.01)
*A61D 7/00* (2006.01)

(52) U.S. Cl.
CPC ............ *A61K 49/0008* (2013.01); *A61D 7/00* (2013.01); *A61D 9/00* (2013.01)

(58) Field of Classification Search
CPC ......... A61K 49/0008; A61D 7/00; A61D 9/00
See application file for complete search history.

(56) References Cited

U.S. PATENT DOCUMENTS

| | | |
|---|---|---|
| 4,233,969 A | 11/1980 | Lock et al. |
| 4,373,519 A | 2/1983 | Errade et al. |
| 4,382,441 A | 5/1983 | Svedman |
| 4,733,659 A | 3/1988 | Edenbaum et al. |
| 4,906,240 A | 3/1990 | Reed et al. |
| 4,969,880 A | 11/1990 | Zamierowski |
| 5,149,331 A | 9/1992 | Ferdman et al. |
| 5,298,015 A | 3/1994 | Komatsuzaki et al. |
| 5,437,651 A | 8/1995 | Todd et al. |
| 5,636,643 A | 6/1997 | Argenta et al. |
| 5,645,081 A | 7/1997 | Argenta et al. |
| 5,911,222 A | 6/1999 | Lawrence et al. |
| 5,921,972 A | 7/1999 | Skow |
| 6,071,267 A | 6/2000 | Zamierowski |
| 6,174,306 B1 | 1/2001 | Fleischmann |
| 6,179,804 B1 | 1/2001 | Satterfield |
| 6,203,563 B1 | 3/2001 | Fernandez |
| 6,287,316 B1 | 9/2001 | Agarwal et al. |
| 6,345,623 B1 | 2/2002 | Heaton et al. |
| 6,398,767 B1 | 6/2002 | Fleischmann |
| 6,553,998 B2 | 4/2003 | Heaton et al. |
| 6,626,891 B2 | 9/2003 | Ohmstede |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,764,462 B2 | 7/2004 | Risk et al. |
| 6,800,074 B2 | 10/2004 | Henley et al. |
| 6,814,079 B2 | 11/2004 | Heaton et al. |
| 6,824,533 B2 | 11/2004 | Risk et al. |
| 6,856,821 B2 | 2/2005 | Johnson |
| 6,936,037 B2 | 8/2005 | Bubb |
| 6,951,553 B2 | 10/2005 | Bubb et al. |
| 7,070,584 B2 | 7/2006 | Johnson et al. |
| 7,108,683 B2 | 9/2006 | Zamierowski |
| 7,381,211 B2 | 6/2008 | Zamierowski |
| 7,699,830 B2 | 4/2010 | Martin |
| 7,976,519 B2 | 7/2011 | Bubb et al. |
| 8,956,335 B2 | 2/2015 | Zamierowski et al. |
| 2006/0228416 A1* | 10/2006 | Faure .................. A61K 9/06 424/486 |
| 2013/0151223 A1* | 6/2013 | Zamierowski ...... G06F 17/5009 703/11 |
| 2015/0157774 A1 | 6/2015 | Zamierowski |

OTHER PUBLICATIONS

Genome Biology 2004, 6:R5 (Year: 2004).*
Huang, et al., "Effect of negative pressure wound therapy on wound healing", Current Problems in Surgery, vol. 51, 2014, 301-331.
Saxena, et al., "Vacuum-Assisted Closure: Microdeformations of Wounds and Cell Proliferation", Plast Reconstr Surg., 114(5), Oct. 2004, 1086-1096.

* cited by examiner

*Primary Examiner* — Robert S Cabral
(74) *Attorney, Agent, or Firm* — Law Office of Mark Brown, LLC; Ryan S. Hinderliter; Mark E. Brown

(57) ABSTRACT

A system and method for evaluating wound healing dressings, treatments, and other variables. The present invention includes in vitro systems and methods for testing wound dressing materials for bacterial control, moisture control, and surface contact properties. The present invention further includes in vivo systems and methods for testing wound dressings, treatments, and other variables utilizing arrays of wound wells on an experimental subject animal. Wound arrays allow for different wound healing variables to be tested with numerous experimental trials within the same subject animal, giving reliable results and reducing the number of subject animals required for testing.

11 Claims, 4 Drawing Sheets

OPTIONAL WELL CONFIGURATION

SYSTEM AND METHOD FOR WOUND ARRAY VARIABLES EVALUATION (WAVE)

BACKGROUND OF THE INVENTION

1. Field of the Invention

The present invention relates generally to testing and evaluating different wound treatment variables.

2. Description of the Related Art

A. External Factors

In the field of wound care, positive healing outcomes are facilitated by a variety of both internal (i.e. patient-subject) and external factors. External factors of interest include: 1) bacterial control, 2) moisture control, and 3) surface contact properties. These and other factors can be manipulated, and the results evaluated, by the system and method according to the present invention, which is disclosed herein. The system and method of the present invention can be applied in a bench-top or an in-vitro manner and also on the external or skin surface of an in vivo animal experimental model.

Properties such as bacterial adherence—the number of bacteria that will adhere to a dressing and the difficulty or ease of removing them by elution techniques—and the growth rates of bacteria in or on a particular dressing material, when compared to rate of growth or doubling time of bacteria in or on a culture medium alone, have direct clinical application. Important considerations include whether bacteria will move up or into a dressing placed on a wound that is contaminated or infected, whether bacteria can be washed away from the field by irrigation through the dressing, and whether bacteria growth and toxic behavior is impeded or enhanced once bacteria are in the dressing.

Properties of moisture control—such as the retention of drainage or moisture versus the loss of moisture from the wound surface by rapid removal to the point of drying—can be assessed in bench top models using such parameters as vapor transmission rates and time to dryness for measured amounts of solutions, such as saline, pure water, colloids and mixtures. Various surfaces can be employed, from porous material mimicking dermis and fibrous wounds (e.g. chamois) to non-porous materials mimicking keratins and other tissue layers. These can be hydrophobic or hydrophilic, absorbent (gels) or non-absorbent materials. Classically, wood and plastic surfaces exhibit very different moisture handling characteristics when used with the same cover dressing material.

Surface contact properties can be predicted from an examination of the surface characteristics of the dressing material and the known behavior of the material. For example, a magnified surface scan of the material shows "pore size." This is known to correlate to both foams and fiber weaves with the ability to "pass through" or retain moisture and drainage. Pore size also correlates to whether the dressing allows ingrowth of granulation tissue (even to the point of incorporation of the dressing layer), which prevents or greatly impedes the ability of the epithelial layer to migrate across the open wound and create "closure" or "healing," or whether the pore size is small enough to prevent ingrowth of granulation and thus favors epithelial migration beneath the dressing. The surface contact properties also influence moisture retention properties and drying properties such that the resulting scab formation, or lack thereof, will either dry into the dressing and become part of it, requiring the epithelium to migrate beneath and through this layer impeding this migration, or it will form an extremely thin scab with moist wound healing properties such that the epithelial migration "streams" readily across the wound, e.g., as disclosed in G. D. Winter U.S. Pat. No. 4,373,519. Thus, if the drying scab is bound to the dressing, its removal can be disruptive or even destructive of the epithelial layer growing beneath it.

Surface contact properties are intimately related to moisture control properties, which, in turn, are intimately related to bacterial control. So, an analysis of single properties can be associated with effects in all three factors of concern. Bench top and/or in vitro studies can give information about all three factors.

B. Bacterial Adherence

Using test tubes with growth or culture media and measured amounts of bacteria (total count or per unit amount), measured amounts of dressing material to be studied can be inserted into the media for specified amounts of time and then removed to measure the amount of bacteria on the material and the residual bacteria in the test tube. Even short or acute time periods are clinically meaningful and can be used to decrease the confounding factor of bacterial doubling during the time of the experiment, but prolonged incubation periods can also reveal much about the interaction of bacteria and the dressing material over time.

A method to test total submersion of materials that may be hydrophobic, or lightweight and tending to "float" and not submerge if left on their own, is to attach a screen to a glass rod (or rod made of the same material as the test tube or container) or to simply expand and flatten the end of a glass rod itself so that it could push the material beneath the surface. The glass rod can be sized so that the desired position beneath the surface is obtained by fixing one end of the rod to the test tube cap so that when the cap is screwed down in place, the rod is the appropriate distance below the surface to force the material into submerged position. After the desired length of time, the material is removed in sterile fashion and a bacterial count is obtained from the residual fluid, giving the difference as the amount absorbed and adhered to the dressing material.

These factors (absorption vs. adherence) are separated by compressing the material against a screen, collecting the absorbed but now compressed out fluid and getting the bacterial count on that. The difference from the original total colony count is the amount adherent to the dressing. This can be confirmed directly by mincing the material thoroughly, plating widely, and doing a colony count or by section and microscopic or histologic staining and counting techniques of measured areas/volumes. Separation techniques such as sonication and elution can also be employed.

Once base lines are obtained, the amount of pressure for submersion—mimicking the compression produced by collapse of surface contact material in a negative pressure wound therapy (NPWT) dressing—can be varied. The immersion/submersion or floating contact can be done with or without agitation (shaking mechanically), centrifugation, sonication, and other mechanical factors. The dressing material(s) can be studied intact or minced to increase surface exposure to define the characteristics that belong to the material specifications and those that correspond to its shape.

C. Bacterial Elution

Once bacterial adherence properties of a material are known, the tightness and permanence, or strength, of the adherence can be tested by evaluating how easily the bacteria can be removed by rinsing or eluting the material. Irrigation, washing, and the simple outward flow of natural moisture and drainage up into an absorbent material having a dry or drying outer layer to ensure continuous upward or outward movement of moisture/drainage are standard clinical means used to remove bacteria from a wound surface. Rinsing or elution testing of the dressing material, once it is impregnated or contaminated with bacteria in a defined or known number, is an important parameter that needs to be measured and known to characterize the behavior of bacterial material. Differing amounts of various elution solutions (starting simply with physiological saline) tested over predetermined time periods can give information by examination and definition of the amount of bacteria in the elution and the amount in the material.

Clinically, a known standard therapy with proven efficacy is to fill a NPWT dressing with a given amount of saline, provide a "dwell time" in minutes, and then suction it out. The elution can be plated, if the amount is small, or run through a filter that would pick up bacteria and then count or plate the bacteria. The material itself can be handled as per the above discussion.

D. Bacterial Growth in Dressing

Once the bacterial absorption and adherence potential of a dressing is known, the subsequent behavior of the bacteria in the dressing material must be determined. Clinically, this determines how frequently a dressing combination needs to be changed or whether it can be left in place and for how long. For example, in the NPWT system by Acelity L.P. Inc. (formerly Kinetic Concepts, Inc.), San Antonio, Tex., there are two very different foam materials. One of the foam materials comes with the option of silver coating and also the option of an attached liner of different wicking and absorption properties. There are several liners or membranes used with the system and available from other sources that change the absorption/bacterial adherence properties and behavior of the system. Several NPWT systems are commercially available.

Once the material to be tested is contaminated or impregnated with bacteria (e.g., introduced on one edge only, introduced by immersion combinations, etc.), growth over time experiments can be performed and the analysis techniques developed above can again be utilized to determine the bacterial count in and on the material (e.g., after a specified number of days). This information is particularly significant because clinically there are questions about the behavior of bacteria over days in and on the material and at the material/wound interface if the physical environment is being changed with such factors and effects as intermittent negative pressure, negative pressure at different levels, irrigation or non-irrigation, etc. Specific inquiries include the effect on toxicity products from the bacteria and the effect on biofilm production.

E. Moisture

The most-used methods for specifying moisture transmission rates of materials are supported by well-established and published test equipment operating procedures and standards for industry and science, and those methods are preferably utilized for standard reporting of "Moisture Vapor Transmission Rates" (MVTR). Because of the multiple combinations of materials and dressings available for use with multiple different NPWT models, other methods to support a summative statement can be analyzed, in addition to the specifications of individual materials. Simple "gravimetric" methods of precisely weighing foam materials before and after use or application steps provide indications of the amount of absorbed and retained drainage. This also applies to in vivo testing. Since many of the in vivo test methods will employ NPWT, a vacuum or suction system that collects and condenses moisture and liquid drainage must be utilized, and simple measurements of this collection rate (corresponding to quantity/time) can be obtained.

This same approach can be applied to in vitro methods that are extended over time. For example, experiments to demonstrate bacterial adherence and elution properties in very short term experiments (e.g., minutes) are discussed above. Bacterial growth over time (e.g., days) also needs to be monitored, and in these experiments, the air above the plate or tube of growth media with implanted material or plated diced material should be controlled so that the aerobic/anaerobic concentration of the overlying gaseous milieu is known. This can be done with either a positive pressure inflow source to a contained growth chamber or with a negative pressure or vacuum source on the outflow side. This outflow vapor can then be "distilled" in cooled, coiled loops to collect moisture or analyzed for moisture vapor and gas use by the organisms. A system can be created which allows measurement of environmental changes reflecting the metabolic changes and uses of the growing organisms as opposed to just measuring bacterial growth as an endpoint. Humidity, temperature and other factors are controlled in the practice of the present invention.

Change in the material itself, in addition to weight gain, is another important consideration for wound treatment variables. Questions include whether magnified examination shows swelling of fibers and spaces; whether moisture is retained as liquid and not just vapor; and whether, for example, moisture or liquid moves by capillary action between relatively intact but closely packed fibers or whether there is absorption by swelling of the spaces between the fibers. Change in the media or material (e.g., tissue in the case of an in vivo application) in contact with the material being examined is also a consideration. This is perhaps easiest explained in the in vivo setting. For example, in pig back experiments, investigatory topics can include the amount of scabbing and dried protein bonding or adherence of the dressing to whichever surface or tissue it was on. A direct visual analog scale can be used to rate and record the amount of drying and moisture retention, from dry scab at one end of the scale to no adherence, moist conditions with no drying, or even moisture retention with visible liquid retention, at the other end of the scale. In vitro we can look for changes in the moisture appearance of the media in which the material is implanted or plated (e.g., does the presence of the material "dry out" the media compared to a control plate), and the volume of residual media and material can be measured after several days in comparison to initial measurements and control tubes. In addition, a dynamic in vitro system can be established in which the dressing is placed on a suitable non-reactive surface and "contained" by a NPWT drape with input and output ports and fluids carefully controlled and measured at each end with the dressing maintained as an active culture medium, bioreactor, or cell or biochemical incubator.

F. Surface Contact

Dennis P. Orgill, M. D., Ph.D., in his writings on NPWT (e.g., Saxena, V. et al., *Vacuum-Assisted Closure: Micro Deformations of Wounds and Cell Proliferation*, Plastic and Reconstructive Surgery, (October 2004), pp. 1086-1096; Huang, C. et al., *Effect of Negative Pressure Wound Therapy on Wound Healing*, Current Problems in Surgery 51 (2014), pp. 301-331) makes the case that one of the mechanisms of action of NPWT is "micro and macro deformation." The tissue in contact with the material deforms to match the surface of the material in contact. For example, Dr. Orgill described the deformation effect of polyurethane ether or the "black foam" (Granufoam brand) of Acelity L.P. Inc. To be a quilting-like effect of the compression by the reticules and the tension of the open pore spaces subjected to negative pressure resulting in a peak and valley tissue surface integrated into the foam which then blocks the ability of the epithelial layer to advance or migrate across this tissue surface.

NPWT can be accurately compared to a "vacuum press" such as those used in industry to seal laminates or veneers to underlying wood. These "press" conditions inside the NPWT dressing are such that any material is held in intimate forceful surface contact relationship to the tissue it is applied to. This results in the ability to augment or enhance the surface characteristics and effects of the material chosen for contact. Thus, one can see how important it is to evaluate the potential and actual surface contact effects of various dressing materials, particularly those that are placed as contact layers or surfaces in NPWT devices where these effects are enhanced by sub-atmospheric (vacuum) pressure.

The clinically understood (cf., Dr. Orgill) micro-deformation effect of open-cell reticulated foam is that this material presents to the surface as alternating spicule or reticule points which penetrate the surface to the branching of the reticules as they weave around and form the cells or pores of the material. That is, they penetrate under the compressive effects of the interior of the NPWT vacuum press to the point on the penetrating strand where the material is no longer an individual strand or vertically or perpendicularly oriented to the surface but is branching or horizontally oriented to the surface.

The degree of penetration can be controlled by the cell or pore size of the foam. The spicules alternate with spaces which communicate with the negative pressure in an open cell foam (the mechanism is different in closed cell material). Thus, the surface of contact with Granufoam material is presented with alternating points of compression and tension in "micro-array" resulting in mechanical induction or "mechano-transduction" of sensing systems sensitive to these forces in the cell. This in turn signals and initiates chemical and metabolic changes in the cell.

As the reporting of the surface feature of dressing material becomes predominantly more frequently expressed as "pore size" related, an old method and a differentiating feature of cotton fiber gauze seems to be becoming lost in this process. The important distinction historically made during the last century for the "pore size" equivalent for gauze is the weave or mesh size, e.g., the number of fibers in the weft and warp per unit area. Fine mesh gauze was originally defined as gauze with a "44/36" weave. That weave was empirically determined to be the cutoff point through which granulation would either grow up into the gauze or be blocked by the closeness of the weave and not penetrate the gauze, thereby allowing epithelialization to proceed beneath the gauze layer. So, by definition "fine mesh gauze" was that with a 44/36 weave and could be used as a "surface" dressing allowing (re)epithelialization beneath it. Coating the hydrophilic gauze with hydrophobic ointments and escharotics of all kinds produced a family of dressings that could produce any effect one desired on the wound surface.

Cotton gauze has largely been supplanted by silks, synthetics, and foams with all degrees of pore size, including microscopic so that the compressed foam surface presents like glass (e.g., Epigard), and with gels and colloids of all degrees of absorption, smoothness, and adhesiveness. The effects of a material on a wound surface can be augmented and enhanced with NPWT. The vacuum press effect also enhances dressing adherence and maintains close apposition over wound and body irregularities, even over large areas. These properties tend to enhance the wound-healing effects of the material.

G. Surface Contact Properties

Examination of the surface of a dressing, by all manner of optics and scanning (e.g., with a scanning electron microscope), can reveal the physical properties and dimensions of protrusions, indentations, and spaces. Pore size is a significant variable factor. It is understood that the surface of a dressing is connected to the interior, and the dressings contact properties are also tied up with the way it handles bacteria and moisture/vapor/drainage. Defining properties such as hydrophilic and hydrophobic relationships to moisture help to predict and understand a dressing's behavior. Defining its ability to wick or move moisture laterally is also important in understanding its function.

SUMMARY OF THE INVENTION

The present invention discloses a system and method for in vitro and in vivo testing and evaluating the bacteria control, moisture control, and surface contact properties of a variety of different wound treatment variables. The system and method can utilize multiple arrays of wells, which can be connected to NPWT systems for evaluating performance with multiple dynamic variables.

BRIEF DESCRIPTION OF THE DRAWINGS

The drawings constitute a part of this specification and include exemplary embodiments of the present invention and illustrate various objects and features thereof.

DETAILED DESCRIPTION OF THE PREFERRED EMBODIMENTS

I. Introduction and Environment

Figure 1:
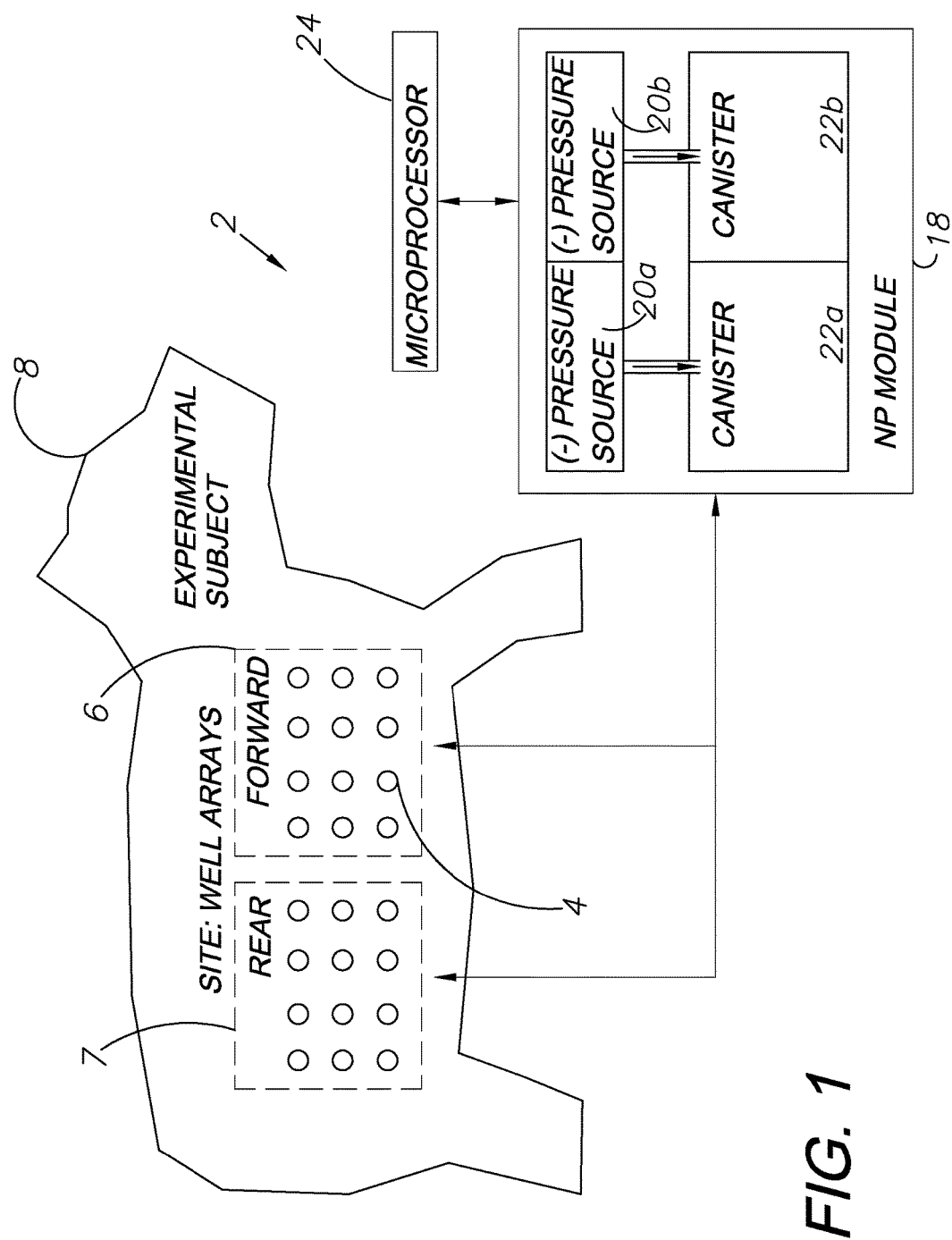
FIG. 1 is a side, elevational view of an array of wells on an experimental subject and a schematic, block diagram of a Wound Array Variables Evaluation (WAVE) system embodying an aspect of the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

II. Wound Array Variables Evaluation (WAVE) Embodiment

In general, after performance of the in vitro tests described above, a wound dressing material can be tested for wound healing properties within a living animal, or in vivo, using the WAVE system of the present invention. In an exemplary embodiment of the present invention, many different wound treatment variables can be effectively tested and evaluated in vivo. Referring to the drawings in more detail, the reference numeral 2 generally designates a wound array variables evaluation (WAVE) system embodying the present invention. In the example shown in FIG. 1, two groupings or arrays, a forward or cephalad array 6 and a rear or caudad array 7, of 6-24 wells 4 are made on each side of an experimental subject animal 8, amounting to four arrays 6 of wells 4 on the animal 8. Alternatively, more or fewer well arrays can be incised or excised into a subject animal 8 as desired. In a preferred embodiment, the animal 8 used is a pig because there are many similarities between pig skin and human skin. However, other animals can alternatively be used. Typically, each well 4 has about a 1 cm diameter circular, or 1 cm per side square, configuration. The wells 4 are scalable larger or smaller as need requires. Full thickness wells 4 are cut to a prescribed depth (e.g., 1 cm) or to the fascia or other identifiable layer on the chosen experimental animal model. Additionally, partial thickness wells 4 can be cut to an approximate depth of several thousandths of an inch, up to about 2 mm to preserve the base of hair follicles and to test wound treatments for shallow or partial thickness wounds.

As shown in FIG. 1, a negative pressure, or vacuum, pump 18 is configured for applying suction to each wound array 6, 7. The pump 18 includes a microprocessor 24 and one or more negative pressure sources 20a,b with corresponding canisters 22a,b configured for disposal of liquids or gases removed from the wound sites 4. The embodiment shown in FIG. 1 shows a negative pressure pump 18 having two negative pressure sources 20a,b and two canisters 22a,b. However, the present invention can be adapted for use with any number of negative pressure sources and canisters.

The wells 4 of the present invention are configured to allow different wound dressing materials 212 to be placed within the wells 4 to test wound healing properties. One or more negative pressure, or vacuum suction, sources 20a,b are configured to provide suction to each of the arrays 6, 7 of wells 4, causing the dressings 212 to compress and provide better surface contact.

Figure 2:
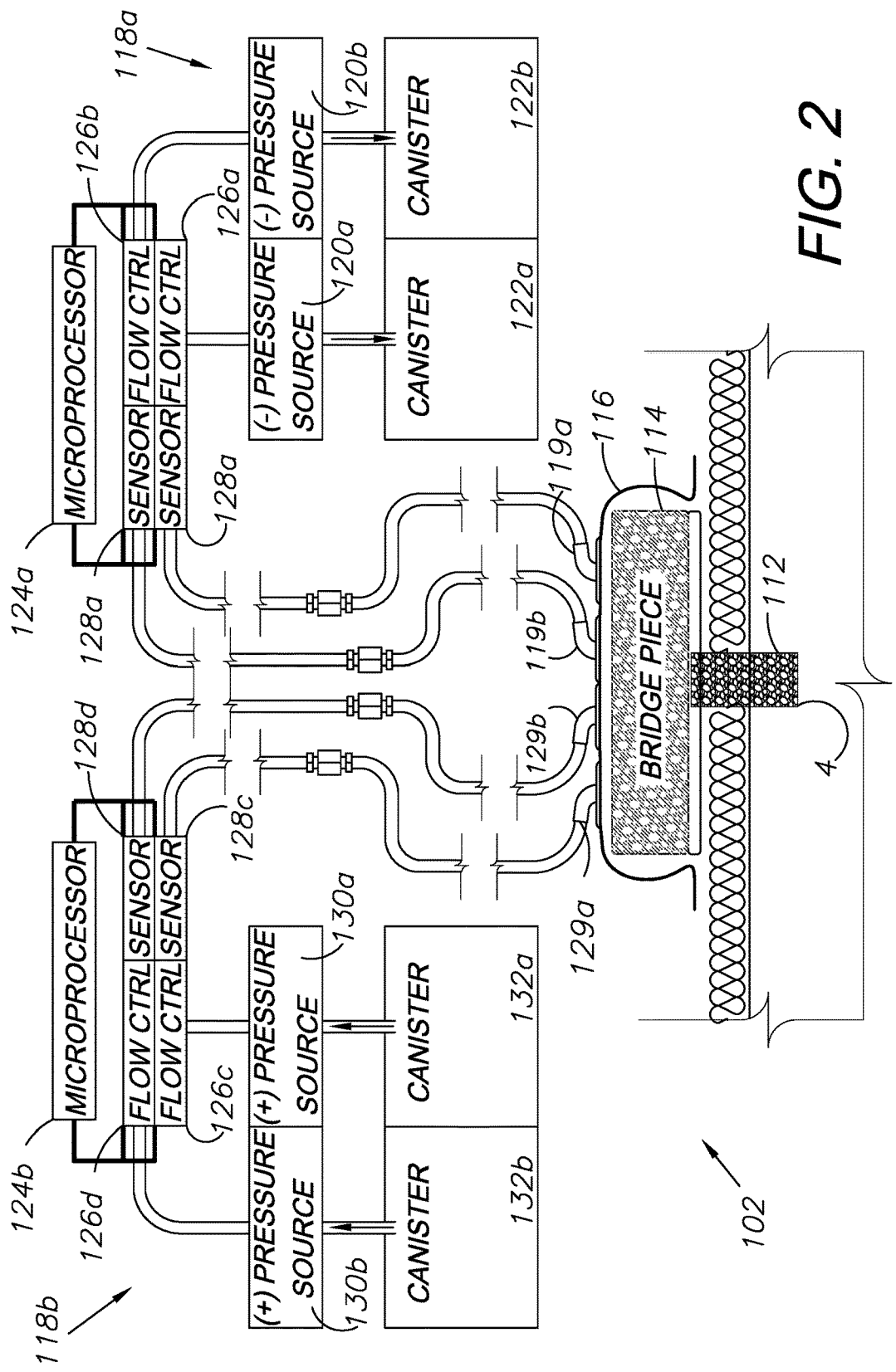
FIG. 2 is a schematic, block diagram of a negative pressure wound therapy (NPWT) system for use with the WAVE system.

The individual wells 4 in an array 6, 7 can be bridged with a fluid transfer component (FTC) 114 (e.g., polyurethane ether or "black foam" (Granufoam brand) of Acelity L.P. Inc.) as shown in FIG. 2. The FTC 114 is covered by a membrane cover layer 116 and, optionally, a liner. Alternative NPWT configurations and constructions are available and suitable for use with the present invention.

Such NPWT dressings typically include: a compressible FTC core configured to compress under negative pressure; a membrane cover layer or drape configured for releasable attachment to a surface and for connection to a negative pressure source; and, optionally, a liner. The liner may be made of, but is not limited to, rayon, absorbent material, wicking material, drying material, gels or colloids, silicone, or mesh. If a pig is being used, compensation can be made to dressing techniques for enhanced adherence to pig skin. For example, pig skin lacks sweat glands and other such adnexae, so compensation may be made to account for altered moisture loss of pig skin. Also, compensation may be made to account for more difficult interference over coarse, growing pig skin. The difficulty of adhering an adhesive overdrape or cover layer because of the coarse nature of pig hair can be overcome, as it is clinically, by utilizing a colloid gel rim under the edge of the drape.

FIG. 2 shows an embodiment of a wound array variables evaluation system 102 including a FTC bridge piece 114 configured for bridging multiple dressings 112 within an array 6 of wound wells 4. In this embodiment, the FTC 114 is covered by a membrane cover layer 116 having input ports 129a,b and output ports 119a,b. The embodiment of the WAVE system 102 in FIG. 2 includes a negative pressure vacuum pump 118a and a positive pressure vacuum pump 118b. Each pump 118a,b includes a microprocessor 124a,b; flow controls 126a,b,c,d; and flow sensors 128a,b,c,d. In this embodiment, the negative pressure vacuum pump 118a includes two negative pressure sources 120a,b with corresponding canisters 122a,b for the disposal of liquids and/or gases removed from the wounds 4. The negative pressure sources 120a,b are connected to output ports 119a,b in the membrane cover layer 116. The positive pressure vacuum pump 118b includes two positive pressure sources 130a,b with corresponding canisters 132a,b configured for holding liquids and/or gases to be introduced to the wounds 4. The positive pressure sources 130a,b are connected to input ports 129a,b in the membrane cover layer 116. The configuration shown in FIG. 2 is merely one embodiment of the invention. Alternatively, any number of pressure sources can be used for the present invention.

Figure 3:
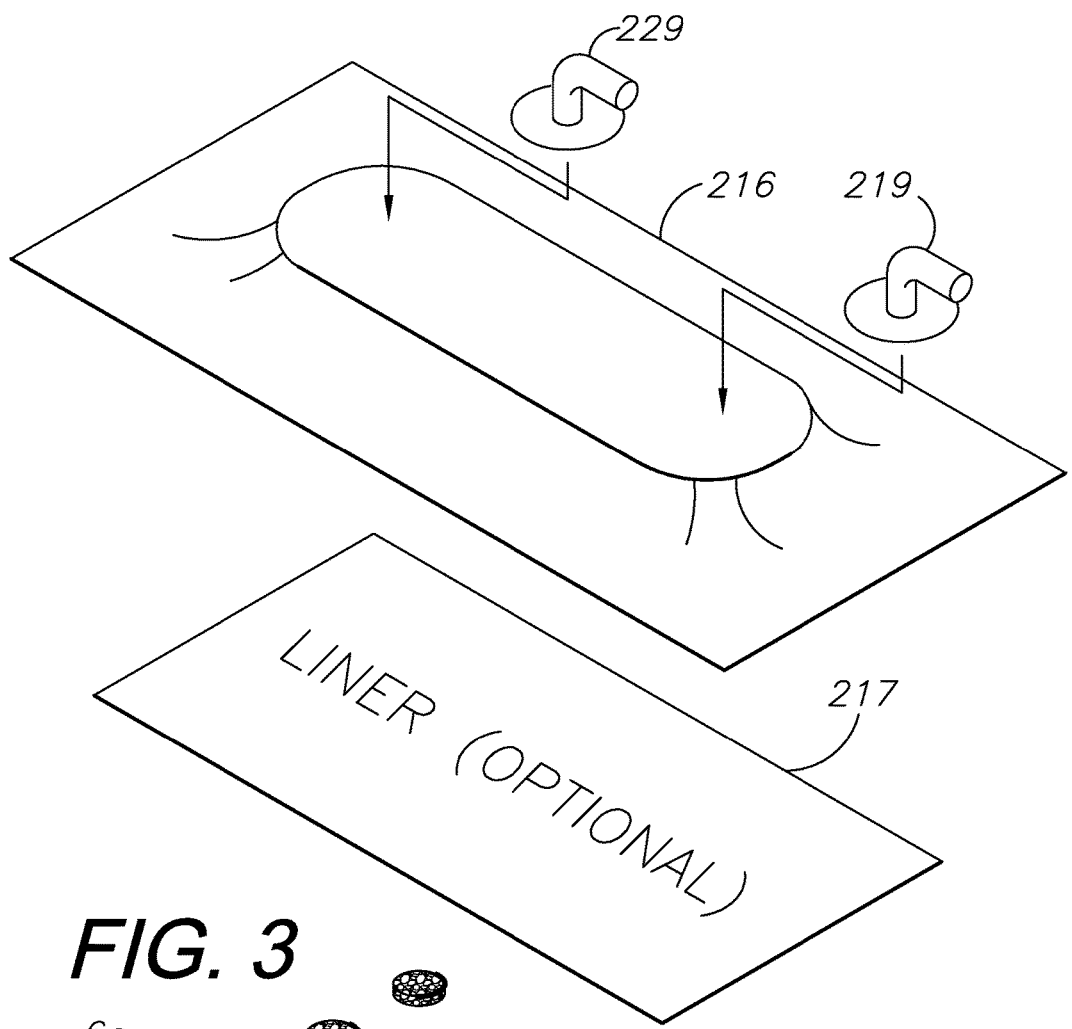
FIG. 3 is an exploded, perspective view of the WAVE system.

FIG. 3 shows wound dressing material 212 for placement within each well 4 within a well array 6. An optional liner 217 and a membrane cover layer 216 are configured for placement over the well array 6. The cover layer 216 includes an input port 229 and an output port 219 configured to be connected to a vacuum. The cover layer 216 can be placed over a fluid transfer component for an optional bridge piece, such as that shown at 114. Alternatively, different numbers and arrangements of input ports, output ports, and vacuums (negative pressure sources) can be used.

The present invention provides an efficient way to test a variety of dressings and wound treatment variables to aid in evaluating different wound treatments for bacterial control, moisture control, and surface contact properties in vivo. This setup allows for experimental controls in the testing. For example, the arrays 6, 7 of wells 4 in the present invention allow for multiple trials of wound treatments within the same animal 8. This process of using a "baseline" array on a single animal or subject can facilitate more accurate and significant experiment results because they can vary significantly from animal to animal (i.e., pig to pig), even with other factors remaining constant. The set-up of arrays 6, 7 on each side of the animal 8 allows comparison of experimental results from both sides of the animal 8. Experimental results from the right and left forward arrays 6 can be compared, and experimental results from the right and left rear arrays 7 can be compared.

Figure 3A:
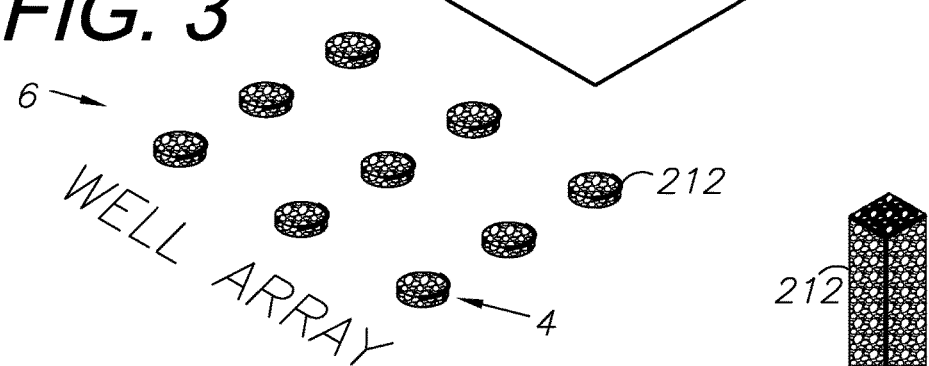
FIG. 3A is a perspective view of an alternative embodiment of dressing material configured for placement within a wound of the WAVE system of the present invention.

FIG. 3A shows one possible configuration of wound dressing material 212 for placement within a wound well 4. However, alternative configurations of dressing material 112, 212 can be used for placement in a well 4. Dressings 112, 212 to be tested are placed within a well 4, sized, and cut to fit. The dressings 112, 212 can be placed alone, in layers, and/or in combinations. The dressings 112, 212 can be tested with or without NPWT. Additionally, forces can be externally applied to the wounds 4 to test for wound healing effects. These forces may include physical, fluidic, or other contact; fluid pressure gradient; pressure wave; osmolar; osmotic; oncotic; mechano/transductive; electromagnetic force (EMF); pharmacological; chemical; anti-microbial; fluidic; bioengineered cells for seeding; thermal; ultrasound; acoustic; and/or other forces. Wound therapies utilizing an implanted bioreactor under a well 4 may also be tested. Additionally, an internal reflector may be implanted under a well 4 and a bioreactor to amplify force waves within the therapy zone for testing the wound healing effects. These wound therapies can be applied continuously or intermittently. This invention is primarily used to test variables for cutaneous wound healing, but other embodiments of the invention may be adapted for healing at different bodily layers or parts of the body.

III. Dynamic Bench-Top Incubator Embodiment

In another embodiment of the present invention, a dynamic, negative pressure dressing is configured for use in bench-top, or in vitro, testing with the dressing being connected to a glass top or other appropriate surface. The dressing includes an input port and an output port at opposite ends. This system may be modified to include multiple input ports and output ports. The negative pressure dressing includes a compressible core, which may be made up of black foam or any other material, manifold, or combination to be tested. The output port, in this embodiment, is connected to a vacuum source and includes P-traps and reservoirs for specimen collection. In an embodiment, the output port is made up of an internal suction tube sealed within a patch and capable of being inserted at various depths and positions inside, or internally into, the manifold material. This configuration allows sampling from various dynamically-created layerings of moisture and exudates. The configuration even allows testing of multiple simultaneous levels by putting multiple channels in the output tubing.

The input tubing, in this embodiment, is configured for being the source of intermittent or continuous media or nutrient ingredients and then bacteria, allowing an active dynamic culturing effect by putting the system in the heat and gas of an incubator, mimicking clinical conditions. The entire system, in this embodiment, is configured to fit within an incubator. Once bacterial growth is established as desired, the system can be irrigated with a solution to be studied and analyzed. This embodiment allows the testing of dressing materials, in bench top fashion, for how much, if any, bacteria are removed from the dressing material with a particular amount of irrigation (i.e., volume times frequency). In this embodiment, the dressing material, irrigation solution, and amount of irrigation can be varied to determine and analyze bacterial removal properties of different materials and solutions.

Figure 4:
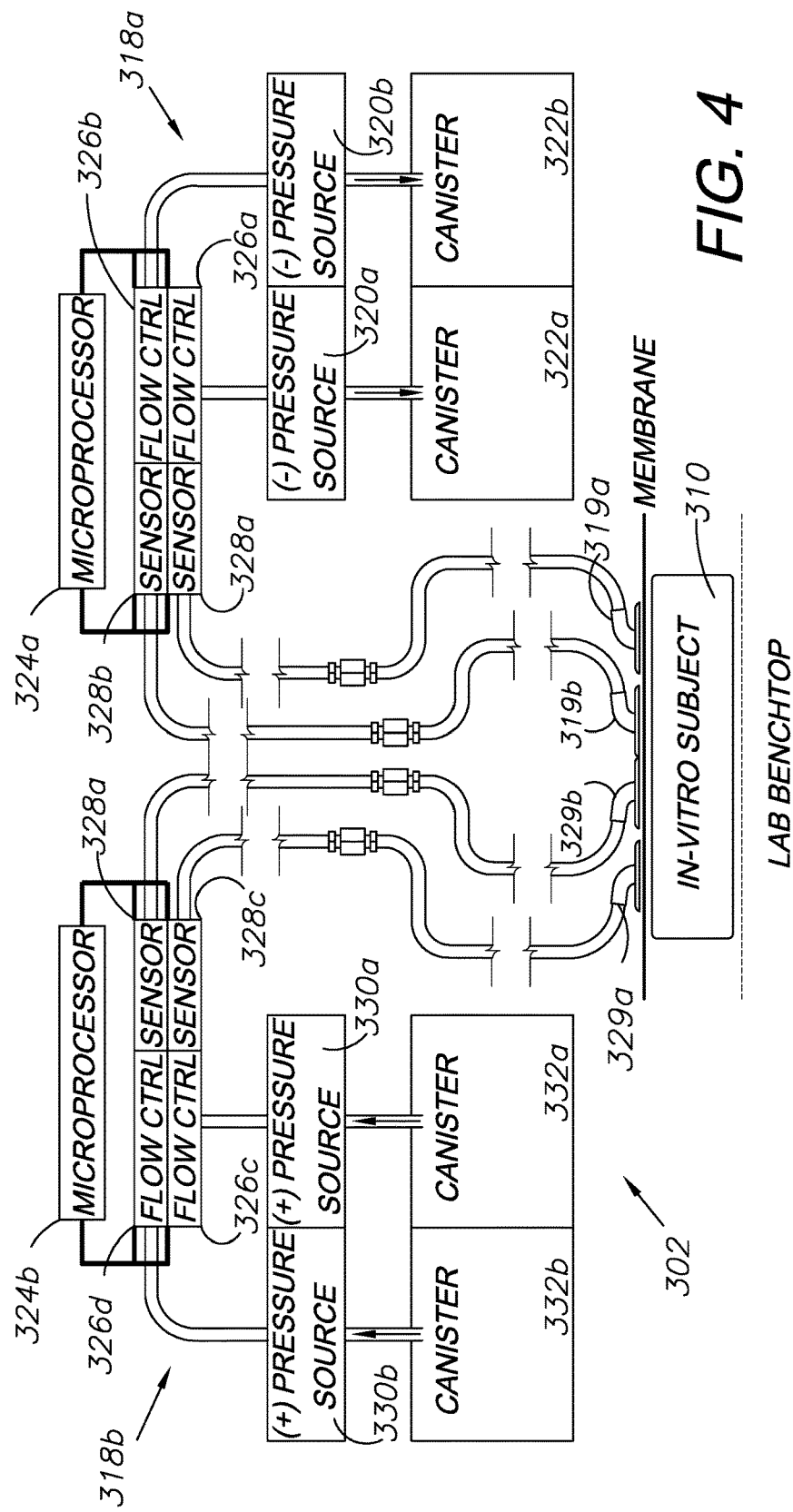
FIG. 4 is a schematic, block diagram of a dynamic bench-top incubator system embodying an aspect of the WAVE system.

FIG. 4 shows an embodiment of a dynamic incubator system 302 configured for connection to an in vitro subject 310. The in vitro subject 310 in this embodiment could be a test tube, Petri dish, or any other bench-top object configured to hold a wound dressing material to be tested. The in vitro subject 310 in this embodiment includes input ports 329a,b and output ports 319a,b connected to a positive pressure vacuum pump 318b and a negative pressure vacuum pump 318a, respectively. Each vacuum pump 318a,b includes a microprocessor 324a,b; flow controls 326a,b,c,d; and flow sensors 328a,b,c,d. In this embodiment, the positive pressure vacuum pump 318b includes two positive pressure sources 330a,b with corresponding canisters 332a,b configured for holding liquids and/or gases to be introduced to the in vitro subject 310 through input ports 329a,b. The positive pressure sources 330a,b are first configured to supply bacteria and growth media into the in vitro subject 310, allowing a dynamic culturing effect in an incubator to mimic clinical conditions. After bacterial growth is established within the dressing in the in vitro subject 310, the positive pressure sources 330a,b are configured to irrigate the in vitro subject 310 with a solution to be studied to test bacterial elution properties of dressings and solutions. The negative pressure pump 318a, in the embodiment of FIG. 4, includes two negative pressure sources 320a,b with corresponding canisters 322a,b configured for the collection and disposal of liquids and/or gases removed from the in vitro subject 310 through output ports 319a,b. Different dressings, irrigation solutions, and types of bacteria can be varied in tests with the dynamic incubator system 302. Alternatively, different amounts of input ports, output ports, and pressure sources can be used.

It is to be understood that the invention can be embodied in various forms, and is not to be limited to the examples discussed above. The range of components and configurations which can be utilized in the practice of the present invention is virtually unlimited.

Having thus described the disclosed subject matter, what is claimed as new and desired to be secured by Letters Patent is:

1. A wound array variables evaluation (WAVE) method comprising the steps of:
   incising or excising a first series of wound wells in a first well array in an experimental subject animal;
   incising or excising a second series of wound wells in a second well array in said experimental subject animal in the same approximate cranial/caudal position on said experimental subject animal as said first well array and in an opposite lateral position on said experimental subject animal from said first well array;
   incising or excising a third series of wound wells in a third well array in said experimental subject animal in a different cranial/caudal position on said experimental subject animal from said first and second well arrays;
   incising or excising a fourth series of wound wells in a fourth well array in said experimental subject animal in the same approximate cranial/caudal position on said experimental subject animal as said third well array and in an opposite lateral position on said experimental subject animal from said third well array;
   wherein said experimental subject animal comprises a pig;
   placing a first wound dressing within or on each wound well in said first well array, accommodating multiple wound healing trials for said first wound dressing on said experimental subject animal;
   placing a second wound dressing within or on each wound well in said second well array, accommodating multiple wound healing trials for said second wound dressing on said experimental subject animal;
   placing a third wound dressing within or on each wound well in said third well array, accommodating multiple wound healing trials for said third wound dressing on said experimental subject animal;
   placing a fourth wound dressing within or on each wound well in said fourth well array, accommodating multiple wound healing trials for said fourth wound dressing on said experimental subject animal;
   wherein one or more of said first, second, third, and fourth wound dressings comprises a control wound dressing, accommodating multiple control wound healing trials on said experimental subject animal;
   placing a first fluid transfer component over said first well array in covering relation over each wound well in said first well array;
   wherein said first fluid transfer component bridges said first wound dressings within each wound well in said first well array for transferring fluid from each said wound well in said first well array;
   placing a second fluid transfer component over said second well array in covering relation over each wound well in said second well array;
   wherein said second fluid transfer component bridges said second wound dressings within each wound well in said second well array for transferring fluid from each said wound well in said second well array;
placing a third fluid transfer component over said third well array in covering relation over each wound well in said third well array;
wherein said third fluid transfer component bridges said third wound dressings within each wound well in said third well array for transferring fluid from each said wound well in said third well array;
placing a fourth fluid transfer component over said fourth well array in covering relation over each wound well in said fourth well array;
wherein said fourth fluid transfer component bridges said fourth wound dressings within each wound well in said fourth well array for transferring fluid from each said wound well in said fourth well array;
placing a first cover layer over said first fluid transfer component and said first well array and attaching said first cover layer to said experimental subject animal;
placing a second cover layer over said second fluid transfer component and said second well array and attaching said second cover layer to said experimental subject animal;
placing a third cover layer over said third fluid transfer component and said third well array and attaching said third cover layer to said experimental subject animal;
placing a fourth cover layer over said fourth fluid transfer component and said fourth well array and attaching said fourth cover layer to said experimental subject animal;
wherein each of said first, second, third, and fourth cover layers includes an adhesive for releasably sealing to said experimental subject animal and a port for connection to a negative pressure source;
connecting said negative pressure source to said first, second, third, and fourth cover layers;
applying negative pressure to one or more of said first, second, third, and fourth well arrays for a predetermined amount of time;
removing said negative pressure;
removing said first, second, third, and fourth cover layers and said first, second, third, and fourth fluid transfer components;
testing and evaluating wound healing properties of said first, second, third, and fourth wound dressings;
comparing wound healing results in said first well array to wound healing results in said second well array; and
comparing wound healing results in said third well array to wound healing results in said fourth well array.

2. The WAVE method of claim 1, wherein:
said first, second, third, and fourth well arrays each include an equal number of wound wells; and
each said equal number of wound wells in each of said first, second, third, and fourth well arrays comprises wound wells in the approximate range of 6 to 24 wound wells per well array, resulting in a total number of wound wells in the approximate range of 24 to 96 wound wells on said experimental subject animal.

3. The WAVE method of claim 1, wherein:
each said wound dressing comprises a wound dressing material and a wound treatment.

4. The WAVE method of claim 3, wherein:
said wound treatment is selected from the group consisting of: applying continuous negative pressure from a negative pressure source, applying intermittent negative pressure from a negative pressure source, applying continuous external pressure waves from a force transducer, applying intermittent external pressure waves from a force transducer, use of a wicking liner, implanting bio-reactors beneath wells, implanting internal wave reflectors beneath wells and bio-reactors, and combinations thereof.

5. A wound array variables evaluation (WAVE) method comprising the steps of:
incising or excising a first series of wound wells in a first well array in an experimental subject animal;
incising or excising a second series of wound wells in a second well array in said experimental subject animal in the same approximate cranial/caudal position on said experimental subject animal as said first well array and in an opposite lateral position on said experimental subject animal from said first well array;
wherein said first and second well arrays each include an equal number of wound wells;
wherein said equal number of wound wells in each of said first and second well arrays comprises wound wells in the range of 6 to 24 wound wells per array;
wherein said experimental subject animal comprises a pig;
placing a first wound dressing within or on each wound well in said first well array, accommodating multiple wound healing trials for said first wound dressing on said experimental subject animal;
placing a second wound dressing within or on each wound well in said second well array, accommodating multiple wound healing trials for said second wound dressing on said experimental subject animal;
placing a fluid transfer component over one or more of said well arrays in covering relation over each wound well in the well array;
wherein said fluid transfer component bridges said wound dressings within each wound well in the covered well array for transferring fluid from each said wound well in the covered well array;
placing a cover layer over said fluid transfer component and said covered well array and attaching said cover layer to said experimental subject animal;
wherein said cover layer includes an adhesive for releasably sealing said cover layer to said experimental subject animal and a port for connection to a negative pressure source;
connecting said negative pressure source to said cover layer;
applying negative pressure to one or more of said well arrays for a predetermined amount of time;
removing said negative pressure, cover layer, and fluid transfer component;
testing and evaluating wound healing properties of said wound dressings; and
comparing wound healing results in said first well array to wound healing results in said second well array.

6. The WAVE method of claim 5, further comprising the steps of:
incising or excising a third series of wound wells in a third well array in said experimental subject animal in a different cranial/caudal position on said experimental subject animal from said first and second well arrays; and
incising or excising a fourth series of wound wells in a fourth well array in said experimental subject animal in the same approximate cranial/caudal position on said experimental subject animal as said third well array and in an opposite lateral position on said experimental subject animal from said third well array.

7. The WAVE method of claim 6, further comprising the steps of:
- placing a third wound dressing within or on each wound well in said third well array, accommodating multiple wound healing trials for said third wound dressing on said experimental subject animal; and
- placing a fourth wound dressing within or on each wound well in said fourth well array, accommodating multiple wound healing trials for said fourth wound dressing on said experimental subject animal.

8. The WAVE method of claim 7, further comprising the step of:
- comparing wound healing results in said third well array to wound healing results in said fourth well array.

9. The WAVE method of claim 7, wherein:
- one or more of said first, second, third, and fourth wound dressings comprises a control wound dressing, accommodating multiple control wound healing trials on said experimental subject animal.

10. The WAVE method of claim 5, wherein:
- each said wound dressing comprises a wound dressing material and a wound treatment.

11. The WAVE method of claim 10, wherein:
- said wound treatment is selected from the group consisting of: applying continuous negative pressure from a negative pressure source, applying intermittent negative pressure from a negative pressure source, applying continuous external pressure waves from a force transducer, applying intermittent external pressure waves from a force transducer, use of a wicking liner, implanting bio-reactors beneath wells, implanting internal wave reflectors beneath wells and bio-reactors, and combinations thereof.

* * * * *